US008703733B2

(12) United States Patent
Wolfe et al.

(10) Patent No.: US 8,703,733 B2
(45) Date of Patent: Apr. 22, 2014

(54) HUMANIZED TTC AND METHODS OF USE THEREOF

(75) Inventors: John H. Wolfe, Blue Bell, PA (US); Carlos Gay-Antaki, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 13/697,885

(22) PCT Filed: May 13, 2011

(86) PCT No.: PCT/US2011/036435
§ 371 (c)(1),
(2), (4) Date: Feb. 20, 2013

(87) PCT Pub. No.: WO2011/143557
PCT Pub. Date: Nov. 17, 2011

(65) Prior Publication Data
US 2013/0143951 A1 Jun. 6, 2013

Related U.S. Application Data

(60) Provisional application No. 61/334,865, filed on May 14, 2010.

(51) Int. Cl.

| | |
|---|---|
| *C12N 9/96* | (2006.01) |
| *C12P 21/00* | (2006.01) |
| *A61K 39/08* | (2006.01) |

(52) U.S. Cl.
USPC .... 514/44 R; 536/23.4; 536/23.7; 435/320.1; 435/69.7; 435/69.8

(58) Field of Classification Search
None
See application file for complete search history.

(56) References Cited

U.S. PATENT DOCUMENTS

| | | | |
|---|---|---|---|
| 5,443,966 | A | 8/1995 | Fairweather et al. |
| 5,571,694 | A | 11/1996 | Makoff et al. |
| 5,780,024 | A | 7/1998 | Brown et al. |
| 7,435,792 | B2 | 10/2008 | Coen et al. |
| 2003/0004121 | A1 | 1/2003 | Coen et al. |
| 2006/0246036 | A1 | 11/2006 | Francis et al. |
| 2009/0226468 | A1 | 9/2009 | Coen et al. |

FOREIGN PATENT DOCUMENTS

| | | |
|---|---|---|
| CN | 1 641 034 B | 4/2010 |
| CN | 101880675 | 11/2010 |
| EP | 0 430 345 A2 | 6/1991 |
| WO | 90/15871 | 12/1990 |
| WO | 2007/012671 | 2/2007 |

OTHER PUBLICATIONS

Francis, J.W., et al. "CuZn superoxide dismutase (SOD-1):tetanus toxin fragment C hybrid protein for targeted delivery of SOD-1 to neuronal cells." J Biol Chem. Jun. 23, 1995;270(25):15434-42.
Li, J., et al. "Insect GDNF:TTC fusion protein improves delivery of GDNF to mouse CNS." Biochem Biophys Res Commun. Dec. 18, 2009;390(3):947-51. Epub Oct. 21, 2009.
Li, J., et al. "Recombinant GDNF: tetanus toxin fragment C fusion protein produced from insect cells." Biochem Biophys Res Commun. Jul. 31, 2009;385(3):380-4. Epub May 22, 2009.

Jiang, K., et al. "A genetic fusion construct between the tetanus toxin C fragment and the lysosomal acid hydrolase beta-glucuronidase expresses a bifunctional protein with enhanced secretion and neuronal uptake." J Neurochem. Jun. 2005;93(5):1334-44.

Kissa, K., et al. "In vivo neuronal tracing with GFP-TTC gene delivery." Mol Cell Neurosci. Aug. 2002;20(4):627-37.

Francis, J.W., et al. "Tetanus toxin fragment C as a vector to enhance delivery of proteins to the CNS." Brain Res. Jun. 11, 2004;1011(1):7-13.

Benn, S.C., et al. "Tetanus toxin fragment C fusion facilitates protein delivery to CNS neurons from cerebrospinal fluid in mice." J Neurochem. Nov. 2005;95(4):1118-31.

Townsend, S.A., et al. "Tetanus toxin C fragment-conjugated nanoparticles for targeted drug delivery to neurons." Biomaterials. Dec. 2007;28(34):5176-84. Epub Sep. 14, 2007.

Makoff, A.J., et al. "Expression of tetanus toxin fragment C in *E. coli*: high level expression by removing rare codons." Nucleic Acids Res. Dec. 25, 1989;17(24):10191-202.

Jiang, K. "Genetic engineering of a therapeutic lysosomal enzyme to improve its delivery into the central nervous system." (Dissertation). University of Pennsylvania, ProQuest, UMI Disserations Publishing. Retrieve from the internet: <URL:http://search.proquest.com/pqdtscieng/docreview/251796152> [Abstract], 2001, p. 1-144.

*Primary Examiner* — Scott Long
*Assistant Examiner* — Arthur S Leonard
(74) *Attorney, Agent, or Firm* — Robert C. Netter, Jr.; Dann, Dorfman, Herrell & Skillman

(57) ABSTRACT

Compositions and methods for treating neurological diseases and disorders are disclosed.

16 Claims, 8 Drawing Sheets

```
   1 AAAAATCTGG ATTGTTGGGT TGATAATGAA GAAGATATAG ATGTTATATT AAAAAGAGT
  61 ACAATTTTAA ATTTAGATAT TAATAATGAT ATTATATCAG ATATATCTGG GTTTAATTCA
 121 TCTGTAATAA CATATCCAGA TGCTCAATTG GTGCCCGGAA TAAATGGCAA AGCAATACAT
 181 TTAGTAAACA ATGAATCTTC TGAAGTTATA GTGCATAAAG CTATGGATAT TGAATATAAT
 241 GATATGTTTA ATAATTTTAC CGTTAGCTTT TGGTTGAGGG TTCCTAAAGT ATCTGCTAGT
 301 CATTTAGAAC AATATGACAC AAATGAGTAT TCAATAATTA GCTCTATGAA AAAATATAGT
 361 CTATCAATAG GATCTGGTTG GAGTGTATCA CTTAAAGGTA ATAACTTAAT ATGGACTTTA
 421 AAAGATTCCG CGGGAGAAGT TAGACAAATA ACTTTTAGGG ATTTATCTGA TAAATTTAAT
 481 GCTTATTTAG CAAATAAATG GGTTTTTATA ACTATTACTA ATGATAGATT ATCTTCTGCT
 541 AATTTGTATA TAAATGGAGT ACTTATGGGA AGTGCAGAAA TTACTGGTTT AGGAGCTATT
 601 AGAGAGGATA ATAATATAAC ATTAAAACTA GATAGATGTA ATAATAATAA TCAATACGTT
 661 TCTATTGATA AATTTAGGAT ATTTTGCAAA GCATTAAATC CAAAAGAGAT TGAAAAATTA
 721 TACACAAGTT ATTTATCTAT AACCTTTTTA AGAGACTTCT GGGGAAACCC TTTACGATAT
 781 GATACAGAAT ATTATTTAAT ACCAGTAGCT TATAGTTCTA AAGATGTTCA ATTGAAAAAT
 841 ATAACAGATT ATATGTATTT GACAAATGCG CCATCGTATA CTAACGGAAA ATTGAATATA
 901 TATTATAGAA GGTTATATAG TGGACTAAAA TTTATTATAA AAAGATATAC ACCTAATAAT
 961 GAAATAGATT CTTTTGTTAG ATCAGGTGAT TTATTAAAT TATATGTATC ATATAACAAT
1021 AATGAGCACA TTGTAGGTTA TCCGAAAGAT GGAAATGCCT TTAATAATCT TGATAGAATT
1081 CTAAGAGTAG GTTATAATGC CCCAGGTATC CCTCTTTATA AAAAAATGGA AGCAGTAAAA
1141 TTGCGTGATT TAAAAACCTA TTCTGTACAA CTTAAATTAT ATGATGATAA AGATGCATCT
1201 TTAGGATTAG TAGGTACCCA TAATGGTCAA ATAGGCAACG ATCCAAATAG GGATATATTA
1261 ATTGCAAGCA ACTGGTACTT TAATCATTTA AAAGATAAAA CTTTAACATG TGATTGGTAC
1321 TTTGTACCTA CAGATGAAGG ATGGACAAAT GATTAA
```

Figure 1

```
   1 GGCGGAGGTA CCGTCGACCT CGAGGAAAGA ACCTGGACTG CTGGGTGGAC AACGAGGAGG
  61 ACATCGACGT GATCCTGAAG AAGAGCACCA TCCTGAACCT GGACATCAAC AACGACATCA
 121 TCAGCGACAT CAGCGGCTTC AACAGCAGCG TGATCACCTA CCCCGACGCC CAGCTGGTGC
 181 CCGGCATCAA CGGCAAGGCC ATCCACCTGG TGAACAACGA GAGCAGCGAG GTGATCGTGC
 241 ACAAGGCCAT GGACATCGAG TACAACGACA TGTTCAACAA CTTCACCGTG AGCTTCTGGC
 301 TGAGAGTGCC CAAGGTGAGC GCCAGCCACC TGGAGCAGTA CGACACCAAC GAGTACAGCA
 361 TCATCAGCAG CATGAAGAAG TACAGCCTGA GCATCGGCAG CGGCTGGAGC GTGAGCCTGA
 421 AGGGCAACAA CCTGATCTGG ACCCTGAAGG ACAGCGCCGG CGAGGTGAGA CAGATCACCT
 481 TCAGAGACCT GAGCGACAAG TTCAACGCCT ACCTGGCCAA CAAGTGGGTG TTCATCACCA
 541 TCACCAACGA CAGACTGAGC AGCGCCAACC TGTACATCAA CGGCGTGCTG ATGGGCAGCG
 601 CCGAGATCAC CGGCCTGGGC GCCATCAGAG AGGACAACAA CATCACCCTG AAGCTGGACA
 661 GATGCAACAA CAACAACCAG TACGTGAGCA TCGACAAGTT CAGAATCTTC TGCAAGGCCC
 721 TGAACCCCAA GGAGATCGAG AAGCTGTACA CCAGCTACCT GAGCATCACC TTCCTGAGAG
 781 ACTTCTGGGG CAACCCCCTG AGATACGACA CCGAGTACTA CCTGATCCCC GTGGCCTACA
 841 GCAGCAAGGA CGTGCAGCTG AAGAACATCA CCGACTACAT GTACCTGACC AACGCCCCCA
 901 GCTACACCAA CGGCAAGCTG AACATCTACT ACAGAAGACT GTACAGCGGC CTGAAGTTCA
 961 TCATCAAGAG ATACACCCCC AACAACGAGA TCGACAGCTT CGTGAAGAGC GGCGACTTCA
1021 TCAAGCTGTA CGTGAGCTAC AACAACAACG AGCACATCGT GGGCTACCCC AAGGACGGCA
1081 ACGCCTTCAA CAACCTGGAC AGAATCCTGA GAGTGGGCTA CAACGCCCCC GGCATCCCCC
1141 TGTACAAGAA GATGGAGGCC GTGAAGCTGA GAGACCTGAA GACCTACAGC GTGCAGCTGA
1201 AGCTGTACGA CGACAAGGAC GCCAGCCTGG GCCTGGTGGG CACCCACAAC GGCCAGATCG
1261 GCAACGACCC CAACAGAGAC ATCCTGATCG CCAGCAACTG GTACTTCAAC CACCTGAAGG
1321 ACAAGACCCT GACCTGCGAC TGGTACTTCG TGCCCACCGA CGAGGGCTGG ACCAACGACT
1381 GACTCGAGGG AGGCGCCGGC GG
```

Figure 2

```
   1 aagaacctgg actgctgggt ggacaacgag gaggacatcg acgtgatcct gaagaagagc
  61 accatcctga acctggacat caacaacgac atcatcagcg acatcagcgg cttcaacagc
 121 agcgtgatca cctaccccga cgcccagctg gtgcccggca tcaacggcaa ggccatccac
 181 ctggtgaaca acgagagcag cgaggtgatc gtgcacaagg ccatggacat cgagtacaac
 241 gacatgttca acaacttcac cgtgagcttc tggctgagag tgcccaaggt gagcgccagc
 301 cacctggagc agtacgacac caacgagtac agcatcatca gcagcatgaa gaagtacagc
 361 ctgagcatcg gcagcggctg gagcgtgagc ctgaagggca caacctgat ctggaccctg
 421 aaggacagcg ccggcgaggt gagacagatc accttcagag acctgagcga caagttcaac
 481 gcctacctgg ccaacaagtg ggtgttcatc accatcacca cgacagact gagcagcgcc
 541 aacctgtaca tcaacggcgt gctgatgggc agcgccgaga tcaccggcct gggcgccatc
 601 agagaggaca caacatcac cctgaagctg gacagatgca caacaacaa ccagtacgtg
 661 agcatcgaca gttcagaat cttctgcaag gccctgaacc ccaaggagat cgagaagctg
 721 tacaccagct acctgagcat caccttcctg agagacttct ggggcaaccc cctgagatac
 781 gacaccgagt actacctgat ccccgtggcc tacagcagca aggacgtgca gctgaagaac
 841 atcaccgact acatgtacct gaccaacgcc cccagctaca caacggcaa gctgaacatc
 901 tactacagaa gactgtacag cggcctgaag ttcatcatca agagatacac ccccaacaac
 961 gagatcgaca gcttcgtgag aagcggcgac ttcatcaagc tgtacgtgag ctacaacaac
1021 aacgagcaca tcgtgggcta ccccaaggac ggcaacgcct tcaacaacct ggacagaatc
1081 ctgagagtgg gctacaacgc ccccggcatc cccctgtaca agaagatgga ggccgtgaag
1141 ctgagagacc tgaagaccta cagcgtgcag ctgaagctgt acgacgacaa ggacgccagc
1201 ctgggcctgg tgggcaccca caacggccag atcggcaacg accccaacag agacatcctg
1261 atcgccagca actggtactt caaccacctg aaggacaaga ccctgacctg cgactggtac
1321 ttcgtgccca ccgacgaggg ctggaccaac gactga
```

Figure 3

LysAsnLeuAspCysTrpValAspAsnGluGluAspIleAspValIleLeuLysLysSer
ThrIleLeuAsnLeuAspIleAsnAsnAspIleIleSerAspIleSerGlyPheAsnSer
SerValIleThrTyrProAspAlaGlnLeuValProGlyIleAsnGlyLysAlaIleHis
LeuValAsnAsnGluSerSerGluValIleValHisLysAlaMetAspIleGluTyrAsn
AspMetPheAsnAsnPheThrValSerPheTrpLeuArgValProLysValSerAlaSer
HisLeuGluGlnTyrAspThrAsnGluTyrSerIleIleSerSerMetLysLysTyrSer
LeuSerIleGlySerGlyTrpSerValSerLeuLysGlyAsnAsnLeuIleTrpThrLeu
LysAspSerAlaGlyGluValArgGlnIleThrPheArgAspLeuSerAspLysPheAsn
AlaTyrLeuAlaAsnLysTrpValPheIleThrIleThrAsnAspArgLeuSerSerAla
AsnLeuTyrIleAsnGlyValLeuMetGlySerAlaGluIleThrGlyLeuGlyAlaIle
ArgGluAspAsnAsnIleThrLeuLysLeuAspArgCysAsnAsnAsnAsnGlnTyrVal
SerIleAspLysPheArgIlePheCysLysAlaLeuAsnProLysGluIleGluLysLeu
TyrThrSerTyrLeuSerIleThrPheLeuArgAspPheTrpGlyAsnProLeuArgTyr
AspThrGluTyrTyrLeuIleProValAlaTyrSerSerLysAspValGlnLeuLysAsn
IleThrAspTyrMetTyrLeuThrAsnAlaProSerTyrThrAsnGlyLysLeuAsnIle
TyrTyrArgArgLeuTyrSerGlyLeuLysPheIleIleLysArgTyrThrProAsnAsn
GluIleAspSerPheValArgSerGlyAspPheIleLysLeuTyrValSerTyrAsnAsn
AsnGluHisIleValGlyTyrProLysAspGlyAsnAlaPheAsnAsnLeuAspArgIle
LeuArgValGlyTyrAsnAlaProGlyIleProLeuTyrLysLysMetGluAlaValLys
LeuArgAspLeuLysThrTyrSerValGlnLeuLysLeuTyrAspAspLysAspAlaSer
LeuGlyLeuValGlyThrHisAsnGlyGlnIleGlyAsnAspProAsnArgAspIleLeu
IleAlaSerAsnTrpTyrPheAsnHisLeuLysAspLysThrLeuThrCysAspTrpTyr
PheValProThrAspGluGlyTrpThrAsnAsp

US 8,703,733 B2

HUMANIZED TTC AND METHODS OF USE THEREOF

This application is a §371 application of PCT/US2011/036435, filed May 13, 2011, which in turn claims priority under 35 U.S.C. §119(e) to U.S. Provisional Patent Application No. 61/334,865, filed on May 14, 2010. The foregoing applications are incorporated by reference herein.

This invention was made with government support under Grant No. NS038690 awarded by the National Institutes of Health. The government has certain rights in this invention.

FIELD OF THE INVENTION

The present invention relates to the field of neurological diseases and disorders. More specifically, the invention provides compositions comprising tetanus toxin C fragment (TTC) for the treatment of neurological diseases and disorders.

BACKGROUND OF THE INVENTION

Several publications and patent documents are cited throughout the specification in order to describe the state of the art to which this invention pertains.

Full citations of these references can be found throughout the specification. Each of these citations is incorporated herein by reference as though set forth in full.

One approach to improve delivery of macromolecules to neurons is to attach a targeting moiety. A good candidate for this is the tetanus toxin C fragment (TTC or B-IIb), which is the atoxic fragment of the tetanus neurotoxin and is responsible for tetanus neurotoxin binding to neurons (Helting et al. (1977) J. Biol. Chem., 252:194-198; Halpern et al. (1993) J. Biol. Chem., 268:11188-11192; Halpern et al. (1995) Curr. Top. Microbiol. Immunol., 195:221-241; Herreros et al. (2000) Biochem. J., 347:199-204). Indeed, due to its atoxic nature and its neuron-specific binding ability, TTC has long been suggested as a potential carrier molecule for protein delivery to the central nervous system (CNS; Bizzini et al. (1977) J. Neurochem., 28:529-542). Chimeric proteins of TTC have been made through either chemical conjugation (Dobrenis et al. (1992) Proc. Natl. Acad. Sci., 89:2297-2301; Francis et al. (1995) J. Biol. Chem., 270:15434-15442; Knight et al. (1999) Eur. J. Biochem., 259:762-769; Schneider et al. (2000) Gene Ther., 7:1584-1592) or genetic fusions (Coen et al. (1997) Proc. Natl. Acad. Sci., 94:9400-9405; Francis et al. (2000) J. Neurochem., 74:2528-2536; Matthews et al. (2000) J. Mol. Neurosci., 14:155-166; Kissa et al. (2002) Mol. Cell Neurosci., 20:627-637). A covalent biochemical conjugate between TTC and the human lysosomal enzyme β-N-acetylhexosaminidase A, which is deficient in GM2 gangliosidoses (Tay-Sachs and Sandhoff diseases), has been shown to be taken up by neurons in culture at a higher level than the wild-type enzyme, reducing GM2 ganglioside storage in neurons in vitro (Dobrenis et al. (1992) Proc. Natl. Acad. Sci., 89:2297-2301). However, for gene therapy, a genetic fusion of the enzyme and TTC is needed to serve as a source for continuous enzyme delivery.

There have been several reports of improved neuronal targeting of cytosolic proteins using genetic fusions with TTC (e.g., Coen et al. (1997) Proc. Natl. Acad. Sci., 94:9400-9405; Coen et al. (1999) Int. J. Dev. Biol. 43:823-830; Figueiredo et al. (1997) Exp. Neurol., 145:546-554; Kissa et al. (2002) Mol. Cell Neurosci., 20:627-637). In contrast, lysosomal enzymes are membrane-inserted proteins that undergo extensive post-translational processing, including N-linked glycosylation, disulfide bond formation and assembly of chains. The glycosylated proteins are phosphorylated at mannose residues and these mannose-6-phophate (M6P) moieties bind to M6P receptors in the trans-Golgi for transport to the acidified compartment of the cell. As even minor modifications to the sequence of lysosomal enzymes can result in retention in the endoplasmic reticulum (ER) or Golgi and loss of function (Neufeld, E. F. (1991) Annu. Rev. Biochem., 60:257-280), it was investigated whether the addition of a TTC moiety to a lysosomal enzyme could result in an enzymatically active fusion protein. Jiang et al. (J. Neurochem. (2005) 93:1334-1344) demonstrated the production and secretion of functional enzymes from fusion constructs between TTC and the lysosomal enzyme β-D-glucuronidase (GUSB), which is defective in mucopolysaccharidosis (MPS) type VII (Sly et al. (1973) J. Ped., 82:249-257). The fusion enzymes had biochemical properties similar to the wild-type GUSB, but they differed significantly from the native GUSB in their distribution between intracellular and secreted compartments. Cross-correction experiments showed that the fusion enzyme was taken up significantly better by neurons than the wild-type protein. The bioavailability of GUSB in the brain of MPS VII mice is limited due to the impermeability of the blood-brain barrier to the protein and the relative lack of abundance of the M6P receptors on neuronal surfaces (Sklar et al. (1992) Endocrinology 130:3484-3491). As TTC undergoes retrograde and trans-synaptic transport to the CNS, the fusion protein can overcome some of the obstacles currently facing effective CNS treatment for MPS VII and other lysosomal storage diseases. For example, it may be possible to deliver the chimeric GUSB across the blood-brain barrier by expressing it in muscles where it may be taken up by neurons (Figueiredo et al. (1997) Exp. Neurol., 145:546-554).

SUMMARY OF THE INVENTION

In accordance with one aspect of the instant invention, nucleic acid molecules encoding a humanized TTC are provided. In a particular embodiment, the humanized TTC sequence comprises SEQ ID NO: 3.

In accordance with another aspect of the instant invention, fusion proteins comprising the humanized TTC and a protein of interest are provided. Nucleic acids encoding the fusion protein are also provided. In a particular embodiment, the protein of interest is a therapeutic protein or a detectable protein. Vectors comprising a nucleic acid sequence encoding the fusion protein of the instant invention are also provided. In a particular embodiment, the vector is an adeno-associated virus. Compositions comprising the vectors of the instant invention and at least one pharmaceutically acceptable carrier are provided.

According to still another aspect of the invention, methods of treating, inhibiting, and/or preventing a neurological disease or disorder are provided. In a particular embodiment, the methods comprise the administration of a composition of the instant invention to a patient in need thereof.

BRIEF DESCRIPTION OF THE DRAWINGS

FIG. 1 provides the nucleotide sequence of bacterial TTC (SEQ ID NO: 1).

FIG. 2 provides the nucleotide sequence of humanized TTC (nucleotides 27-1382) plus two flanking sequences comprising Xho I sites to facilitate cloning (SEQ ID NO: 2).

FIG. 3 provides the nucleotide sequence of humanized TTC (SEQ ID NO: 3).

FIG. 4 provides the amino acid sequence of TTC (SEQ ID NO: 4).

FIG. 6 shows GUSB activity after a single injection into the left hippocampus of AAV9 expressing humanized GUSB-TTC (GTCL) vs. wild-type GUSB.

DETAILED DESCRIPTION OF THE INVENTION

Figure 5A:
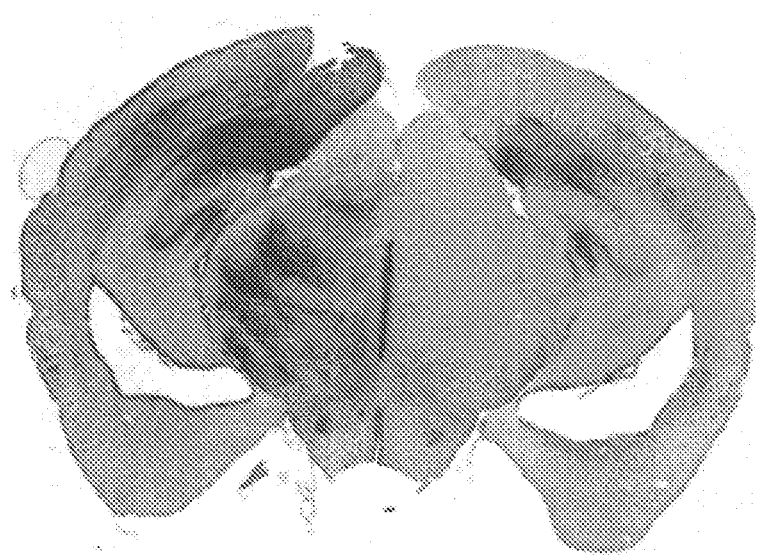
FIGS. 5A and 5B provide images of two different mouse brain slices from mice injected with adeno-associated virus (AAV) vectors encoding humanized TTC fused to β-glucuronidase. Dark staining indicates β-glucuronidase enzymatic activity.

The bacterial derived C fragment of tetanus toxin (TTC) is known to bind to neurons and can be engineered to carry reporter proteins such as green fluorescent proteins and β-galactosidase. Fusion proteins comprising TTC and eukaryotic proteins or enzymes have been produced and the resultant products have demonstrated all of the important functional and chemical features of the wild-type protein/enzyme. Attempts to synthesize viral vectors comprising nucleic acids encoding the fusion protein have previously produced lower yields and the viral vectors failed to produce enzymatic activity in vivo. The instant invention has demonstrated that using codons that are more abundantly utilized in eukaryotic (particularly human) cells resulted in a high titer vector that yields high production of enzyme distributed over a larger area of the CNS, particularly the brain. Approximately one-third of the codons of the nucleic acid encoding TTC were changed while maintaining the same encoded for amino acid. While the instant application focuses on humanizing TTC (i.e., using codons that are more abundantly utilized in humans), other bacterial or non-human proteins may be humanized to increase expression in human cells and increase titers of viral vectors comprising nucleic acids encoding the humanized protein.

Neurogenetic diseases have widespread lesions in the CNS. This presents a problem for treatment because it requires methods that can treat widespread areas. As stated hereinabove, the tetanus toxin fragment C (TTC) is a neurotropic carrier that has been fused to reporter proteins such as β-galactosidase and green fluorescent protein and to therapeutic proteins such as superoxide dismutase and glial derived neurotrophic factor. However, the methods using TTC have been previously limited to protein delivery models. It has also been previously shown that a fusion protein between TTC and the lysosomal enzyme β-glucuronidase (GUSB) has biochemical properties similar to the wild-type enzyme, but different secretion profiles, demonstrating the bi-functionality of the chimeric molecule. Furthermore, it has been shown that this fusion protein can be synthesized in mammalian cells.

Herein, humanized TTC fused to the lysosomal enzyme GUSB has been successfully introduced into a functional adeno-associated virus (AAV) vector. The results show unprecedented levels of enzymatic activity 1 month post-injection in the CNS of mice after a single injection of 1 μl of vector into the dentate gyrus, compared to experiments using the wild-type enzyme. Without being bound by theory, the increased enzymatic activity may at least in part be due to proper post-translational modifications of the enzyme (e.g., N-glycolsylations) being produced in mammalian cells. The ability of the fusion protein to enter the CNS after an intramuscular injection of the vector was also tested using the hypoglossal pathway as a model. The results show that the fusion protein is able to bypass the blood brain barrier (BBB) and deliver the therapeutic enzyme into the expected nuclei in the CNS. This shows that inserting a TTC fusion construct into an AAV vector can be used in gene therapy for diseases that affect the CNS by delivering the vector directly in the brain, in which case TTC is distributed widely via neurons, or by injecting muscle and allowing for the protein to bypass the BBB through the axonal transport of TTC in motor neurons. This method of TTC fusion protein delivery eliminates the need for repeated delivery of fused protein, as in previous models, as it is being continuously synthesized in vivo.

In accordance with the instant invention, novel TTC sequences are provided. According to one aspect of the instant invention, fusion proteins comprising TTC and a protein of interest are provided, as well as nucleic acids encoding the same. The C-terminus of the protein of interest may be attached to the N-terminus of TTC within the fusion protein, i.e., the TTC nucleotide sequence may be cloned in-frame and 3' to a nucleic acid molecule encoding the protein of interest. In a particular embodiment, the protein of interest is attached to TTC by an amino acid linker (e.g., from about 1 to about 50 amino acids, more particularly about 1 to about 20 amino acids or about 1 to about 10 amino acids).

In another embodiment, the humanized TTC nucleic acid of the instant invention has at least 70%, 80%, 90%, 95%, 97%, 99%, or 100% identity with SEQ ID NO: 3, particularly at least 95%, 97%, or 99% identity. In a particular embodiment, the humanized TTC nucleic acid encodes a protein having at least 90%, 95%, 97%, 99%, or 100% identity with SEQ ID NO: 4. In still another embodiment, the humanized TTC is SEQ ID NO: 3.

In a particular embodiment of the instant invention, the protein of interest in the fusion protein is a therapeutic protein (e.g., neurological therapeutic protein). In a particular embodiment, the protein of interest is a cytosolic protein. In a particular embodiment, the protein of interest is a lysosomal enzymes or a membrane-inserted protein. A therapeutic protein affects amelioration and/or cure of a disease, disorder, pathology, and/or the symptoms associated therewith. The proteins may have therapeutic value against neurological disorders (particularly of the CNS) including, without limitation, neurological degenerative disorders, Alzheimer's disease, Parkinson's disease, Huntington's disease (HD), stroke, trauma, infections, meningitis, encephalitis, gliomas, cancers (including brain metastasis), HIV-1 associated dementia (HAD), HIV associated neurocognitive disorders (HAND), paralysis, amyotrophic lateral sclerosis (ALS or Lou Gerhig's disease), multiple sclerosis (MS), CNS-associated cardiovascular disease, prion disease, obesity, metabolic disorders, inflammatory disease, metabolic disorders, and lysosomal storage diseases (LSDs; such as, without limitation, Gaucher's disease, Pompe disease, Niemann-Pick, Hunter syndrome (MPS II), Mucopolysaccharidosis I (MPS I), GM2-gangliosidoses, Gaucher disease, Sanfilippo syndrome (MPS MA), Tay-Sachs disease, Sandhoff's disease, Krabbe's disease, metachromatic leukodystrophy, and Fabry disease). Therapeutically active proteins include, but are not limited to, enzymes, antibodies, hormones, growth factors, other polypeptides, which administration to neurons can effect amelioration and/or cure of a disease, disorder, pathology, and/or the symptoms associated therewith. Neuroactive polypeptides useful in this invention include but are not limited to endocrine factors, growth factors, hypothalamic releasing factors, neurotrophic factors, paracrine factors, neurotransmitter polypeptides, antibodies and antibody fragments which bind to any of the above polypeptides (such as neurotrophic factors, growth factors, and others), antibodies and antibody fragments which bind to the receptors of these polypeptides (such as neurotrophic factor receptors), cytokines, endorphins, polypeptide antagonists, agonists for a receptor expressed by a CNS cell, polypeptides involved in lysosomal storage diseases, and the like. In a particular embodiment, the therapeutic protein exerts its effect on the CNS.

Examples of specific therapeutic proteins include, without limitation, β-glucuronidase (e.g., for the treatment of lysosomal storage disorders), catalase, telomerase, superoxide dismutase (SOD), glutathionperoxidase, glutaminase, cytokines, endorphins (e.g., enkephalin), growth factors (e.g., epidermal growth factor (EGF)), acidic and basic fibroblast growth factor (aFGF and bFGF), insulin-like growth factor I (IGF-I; see, e.g., Oppenheim, R. W. (1996) Neuron 17:195-197; Thoenen et al. (1993) Exp. Neurol., 124:47-55; and Henderson, C. E. (1995) Adv. Neurol., 68:235-240), brain-derived neurotrophic factor (BDNF), glial-derived neurotrophic factor (GDNF; see, e.g., Li et al. (2009) Biochem. Biophys. Res. Comm., 390:947-951), neurotrophin-3 (NT-3), NT-4/5, protease nexin I (PNI; e.g., for the treatment of Alzheimer disease (Houenou et al. (1995) PNAS 92:895-899)), serine protease inhibitor protein (SPI3; e.g., Safaei, R. (1997) Brain Res Dev Brain Res., 100: 5-12), platelet derived growth factor (PDGF), vascular growth factor (VGF), nerve growth factor (NGF), insulin-like growth factor-II (IGF-II), tumor necrosis factor-B (TGF-B), survival motor neuron (SMN; e.g., for the treatment of spinal muscular atrophy; Lefebvre et al. (1995) Cell 80:155-165; Roy et al. (1995) Cell 80:167-178), leukemia inhibitory factor (LIF), anti-apoptotic proteins (e.g., BCL-2, PI3 kinase), amyloid beta binders (e.g. antibodies), butyrylcholinesterase or acetylcholinesterase (e.g., Carmona et. al. (1999) Drug Metab. Dispos., 28:367-371; Carmona (2005) Eur. J. Pharmacol., 517:186-190), modulators of α-, β-, and/or γ-secretases, vasoactive intestinal peptide, leptin, acid alpha-glucosidase (GAA), acid sphingomyelinase, iduronate-2-sultatase (I2S), α-L-iduronidase (IDU), β-Hexosaminidase A (HexA), β-N-acetylhexosaminidase A Acid β-glucocerebrosidase, N-acetylgalactosamine-4-sulfatase, α-galactosidase A, and neurotransmitters (see, e.g., Schapira, A. H. (2003) Neurology 61:S56-63; Ferrari et al. (1990) Adv Exp Med Biol. 265:93-99; Ferrari et al. (1991) J Neurosci Res. 30:493-497; Koliatsos et al. (1991) Ann Neurol. 30:831-840; Dogrukol-Ak et al. (2003) Peptides 24:437-444; Amalfitano et al. (2001) Genet Med. 3:132-138; Simonaro et al. (2002) Am J Hum Genet. 71:1413-1419; Muenzer et al. (2002) Acta Paediatr Suppl. 91:98-99; Wraith et al. (2004) J. Pediatr. 144:581-588; Wicklow et al. (2004) Am J Med Genet. 127A:158-166; Grabowski (2004) J. Pediatr. 144:S15-19; Auclair et al. (2003) Mol Genet Metab. 78:163-174; Przybylska et al. (2004) J Gene Med. 6:85-92). In a particular embodiment, the therapeutic protein is β-glucuronidase.

In yet another embodiment, the protein of interest is a detectable protein. Detectable proteins include, without limitation, fluorescent proteins (e.g., GFP), horseradish peroxidase, urease, alkaline phosphatase, glucoamylase, ferritin, dopamine receptor, and β-galactosidase.

The nucleic acids of the instant invention may be delivered to a cell by any known method. For example, the nucleic acids can be delivered via synthetic delivery systems or nanoparticles. In a particular embodiment, the nucleic acid molecule encoding the fusion protein of the instant invention may be contained with a vector (e.g., a single stranded vector). The vector may be a viral vector, such as, without limitation, lentiviral, retroviral, herpesviral, and adenoviral vectors. In a particular embodiment, the vector is an AAV vector. The AAV vector can be of any AAV serotype. For example, the AAV vector can be, without limitation, AAV-1, AAV-2, AAV-3, AAV-4, AAV-5, AAV-6, AAV-7, AAV-8, AAV-9, etc., or hybrid vectors combining characteristics of more than one AAV serotype. AAV vectors can have one or more of the AAV wild-type genes deleted in whole or part (e.g., the rep and/or cap genes). In a particular embodiment, the AAV vectors retain at least those sequences required in cis for replication and packaging (e.g., functional flanking ITR sequences which assist in the rescue, replication, and packaging of the AAV virion).

As stated hereinbelow, methods of treating a neurological disease or disorder in a patient are provided. In a particular embodiment, the method comprises administering to a patient in need thereof at least one composition comprising at least one vector (e.g., viral vector) of the instant invention and at least one pharmaceutically acceptable carrier. In a particular embodiment, the method comprises administering to a patient in need thereof at least one composition comprising at least one fusion protein (e.g., synthesized in mammalian (e.g., human) cells) of the instant invention and at least one pharmaceutically acceptable carrier. Examples of neurological diseases and disorders include, without limitation, multi-infarct dementia, stroke, trauma, infections, meningitis, encephalitis, Pick's Disease, frontal lobe degeneration, corticobasal degeneration, multiple system atrophy, progressive supranuclear palsy, Creutzfeldt-Jakob disease, Lewy body disease, neuroinflammatory disease, spinal muscular atrophy, Parkinson's Disease, Alzheimer's Disease, amyotrophic lateral sclerosis, neuroAIDS, Chron's Disease, Huntington's Disease, gliomas, cancers (including brain metastasis), HIV-1 associated dementia (HAD), HIV associated neurocognitive disorders (HAND), paralysis, multiple sclerosis (MS), CNS-associated cardiovascular disease, prion disease, metabolic disorders, and lysosomal storage diseases (LSDs). In a particular embodiment of the instant invention, the neurological disease is a lysosomal storage disease such as, without limitation, Gaucher's disease, Pompe disease, Niemann-Pick, Hunter syndrome (MPS II), Mucopolysaccharidosis I (MPS I), GM2-gangliosidoses, Gaucher disease, Sanfilippo syndrome (MPS IIIA), Tay-Sachs disease, Sandhoff's disease, Krabbe's disease, metachromatic leukodystrophy, and Fabry disease. The methods of the instant invention may be co-administered with any other therapeutic method for the treatment of the neurological disease or disorder.

I. Definitions

The following definitions are provided to facilitate an understanding of the present invention:

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" may refer to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$Tm=81.5° C.+16.6 \text{ Log } [Na+]+0.41(\% \ G+C)-0.63(\% \text{ formamide})-600/\#bp \text{ in duplex}$$

As an illustration of the above formula, using $[Na+]=[0.368]$ and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. For example, hybridizations may be performed, according to the method of Sambrook et al. using a hybridization solution comprising: 5×SSC, 5×Denhardt's reagent, 1.0% SDS, 100 μg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37.0 in 1×SSC and 1% SDS; (4) 2 hours at 42-65° in 1×SSC and 1% SDS, changing the solution every 30 minutes.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1× SSC and 0.5% SDS at 65° C. for 15 minutes.

The term "percent identity" refers to the percentage of sequence identity found in a comparison of two or more nucleic acid sequences. Percent identity can be determined by standard alignment algorithms, for example, the Basic Local Alignment Search Tool (BLAST) described by Altshul et al. (J. Mol. Biol. (1990) 215:403-10) as well as GAP, BESTFIT, FASTA, and TFASTA (available as part of the GCG® Wisconsin Package® (Accelrys Inc., Burlington, Mass.)).

A "vector" is a replicon, such as a plasmid, cosmid, bacmid, phage or virus, to which another genetic sequence or element (either DNA or RNA) may be attached so as to bring about the expression and/or replication of the attached sequence or element.

The term "gene" refers to a nucleic acid comprising an open reading frame encoding a polypeptide, including exon and (optionally) intron sequences. The nucleic acid may also optionally include non-coding sequences such as promoter or enhancer sequences. The term "intron" refers to a DNA sequence present in a given gene that is not translated into protein and is generally found between exons.

The phrase "operably linked," as used herein, may refer to a nucleic acid sequence placed into a functional relationship with another nucleic acid sequence. Examples of nucleic acid sequences that may be operably linked include, without limitation, promoters, cleavage sites, purification tags, transcription terminators, enhancers or activators and heterologous genes which when transcribed and, if appropriate to, translated will produce a functional product such as a protein, ribozyme or RNA molecule. The phrase "operably linked" may also, for example, refer to a nucleic acid sequence encoding a protein of interest placed in functional relationship with a nucleic acid encoding the carboxy-terminal domain of a Ubl such that the catalytic cleavage activity of the carboxy-terminal domain of a Ubl in proteinaceous form leads to the release of the protein of interest.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Polypeptide" and "protein" are sometimes used interchangeably herein and indicate a molecular chain of amino acids. The term polypeptide encompasses peptides, oligopeptides, and proteins. The terms also include post-expression modifications of the polypeptide, for example, glycosylations, acetylations, phosphorylations and the like. In addition, protein fragments, analogs, mutated or variant proteins, fusion proteins and the like are included within the meaning of polypeptide.

The term "isolated" may refer to protein, nucleic acid, compound, or cell that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HC1, acetate, phosphate), water, aqueous solutions, oils, bulking substance (e.g., lactose, mannitol), excipient, auxiliary agent or vehicle with which an active agent of the present invention is administered. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

The term "treat" as used herein refers to any type of treatment that imparts a benefit to a patient afflicted with a disease, including improvement in the condition of the patient (e.g., in one or more symptoms), delay in the progression of the condition, etc.

A "therapeutically effective amount" of a compound or a pharmaceutical composition refers to an amount effective to prevent, inhibit, treat, or lessen the symptoms of a particular disorder or disease. The treatment of a neurological disease or disorder herein may refer to curing, relieving, inhibiting, and/or preventing the neurological disease or disorder, a symptom(s) of it, or the predisposition towards it.

II. Administration

As stated hereinabove, any gene delivery system may be used to deliver the nucleic acid molecules of the instant invention to a cell and/or patient. For simplicity, the following description exemplifies the use of viral vectors, but other gene delivery vehicles (e.g., nanoparticles and synthetic delivery systems) may be used in accordance with the description below.

As stated hereinabove, viral vectors, particularly AAV vectors, comprising a nucleic acid encoding the fusion protein of the instant invention are provided. Compositions comprising at least one viral vector of the instant invention and at least one pharmaceutically acceptable carrier are also encompassed by the instant invention.

The instant invention encompasses methods of treating a neurological disorder comprising the administration of a composition comprising the viral vectors of the instant invention and at least one pharmaceutically acceptable carrier to a in a patient in need thereof. The term "patient" as used herein refers to human or animal (particularly mammalian) subjects.

The viral vectors of the invention may be conveniently formulated for administration with any pharmaceutically acceptable carrier. For example, the viral vectors may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the viral vectors in the chosen medium may be varied and the medium may be chosen based on the desired route of administration of the pharmaceutical preparation. Except insofar as any conventional media or agent is incompatible with the viral vector to be administered, its use in the pharmaceutical preparation is contemplated.

The dose and dosage regimen of the compositions according to the invention that are suitable for administration to a particular patient may be determined by a physician/veterinarian/medical specialist considering the patient's age, sex, weight, general medical condition, and the specific condition for which the viral vector is being administered and the severity thereof. The physician/veterinarian/medical specialist may also take into account the route of administration, the pharmaceutical carrier, and the viral vector's biological activity.

Selection of a suitable pharmaceutical preparation will also depend upon the mode of administration chosen. The pharmaceutical preparation comprises the viral vector preferably dispersed in a medium that is compatible with the site of injection.

Viral vectors of the instant invention may be administered by any method such as intravenous injection into the blood stream, oral administration, or by subcutaneous, intracranial, intramuscular or intraperitoneal injection. The viral vector of the invention may be administered by direct injection into an area proximal to or across the blood brain barrier. In a particular embodiment, the composition comprising the viral vector is administered directly to or to an area proximal to a neuron(s). In a particular embodiment, the composition comprising the viral vector is administered directly to the brain. In yet another embodiment, the composition comprising the viral vector is administered intramuscularly. Pharmaceutical preparations for injection are known in the art. If injection is selected as a method for administering the viral vectors, steps must be taken to ensure that sufficient amounts of the viral vectors reach their target cells to exert a biological effect.

Pharmaceutical compositions containing a viral vector the present invention as the active ingredient in intimate admixture with a pharmaceutically acceptable carrier can be prepared according to conventional pharmaceutical techniques. The carrier may take a wide variety of forms depending on the form of preparation desired for administration, e.g., intravenous, direct injection, intracranial, and intramuscular.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of viral vectors may be determined by evaluating the toxicity of the molecules or cells in animal models. Various concentrations of viral vectors in pharmaceutical preparations may be administered to mice or other animals, and the minimal and maximal dosages may be determined based on the beneficial results and side effects observed as a result of the treatment. Appropriate dosage unit may also be determined by assessing the efficacy of the viral vector treatment in combination with other standard drugs. The dosage units of viral vector may be determined individually or in combination with each treatment according to the effect detected.

The following examples are provided to illustrate various embodiments of the present invention. The examples are illustrative and are not intended to limit the invention in any way.

EXAMPLE 1

AAV vectors encoding a fusion protein comprising β-glucuronidase and TTC were generated. The titer obtained with a first AAV vector backbone (pTR-UF4; University of Florida) encoding a fusion protein comprising β-glucuronidase and bacterial TTC were $1.0 \times 10^{11}$. In stark contrast, the titers obtained with a second AAV vector backbone (pZAC; University of Pennsylvania) encoding a fusion protein comprising β-glucuronidase and the humanized TTC of the instant invention was $2 \times 10^{13}$. The helper plasmids were the same for both preparations and the serotype of the capsid for the first backbone was AAV2 and the capsid for the second backbone was AAV1. The observed difference in titer is significantly greater than the difference in titer observed between the first AAV vector backbone ($3-5 \times 10^{12}$) and the second AAV vector backbone ($3-5 \times 10^{13}$) with other inserts.

Figure 5B:
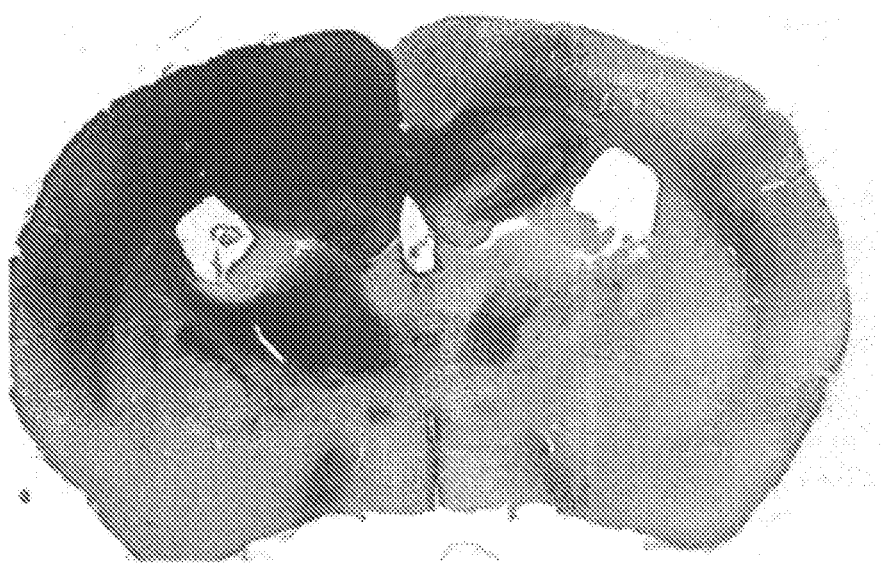

The humanized TTC sequence was cloned in frame at the 3' end of the human β-glucuronidase (GUSB) cDNA to create a fusion protein. High titer AAV vector was made with serotype 1 cap protein. A single injection (1 microliter) of vector virus was injected into the mouse hippocampus on one side of the brain. The brain was perfused, fixed, and sectioned at 1 month post-injection. The dark stain is GUSB enzymatic reaction at 2 different levels of the brain, showing much wider spread of the enzyme than occurs with wild-type enzyme (FIG. 5). GUSB enzymatic activity can also be observed 3 months post-injection covering most of the brain.

EXAMPLE 2

The non-toxic C fragment of tetanus toxin (TTC) can function as a carrier moiety for a cytosolic reporter gene such as GFP to be transported retrograde and to cross to a second order neuron (Lalli et al. (2002) J. Cell Biol., 156:233-9; Kissa et al. (2002) Mol. Cell Neurosci., 20:627-37). The ability of a GUSB-TTC fusion protein to enhance enzyme delivery was evaluated. Several variants of fusion sequences were generated and one was selected that produced high levels of GUSB in transfected MPS VII mouse cells and secreted a stable fusion protein into the medium (Jiang et al. (2005) J. Neurochem., 93:1334-44). However, the ability to generate an AAV vector to evaluate transport of the fusion protein in neuronal pathways was slowed by the inability to grow a high-titer vector. As explained hereinabove, this was resolved by converting the TTC sequence to a sequence optimized for human codon usage. Without being bound by theory, a secondary structure may form in the single stranded viral genome of AAV encoding wild-type TTC that reduces efficiency of replication, thereby lowering the titer significantly with wild-type TTC. The instant "humanization" involves changing about ⅓ of the bases in the 1100 bp sequence, which were scattered throughout the sequence. Unexpectedly, this humanized sequence enables the production of a very high titer vector ($>10^{13}$ GC/ml), which may be used for in vivo studies.

Figure 6A:
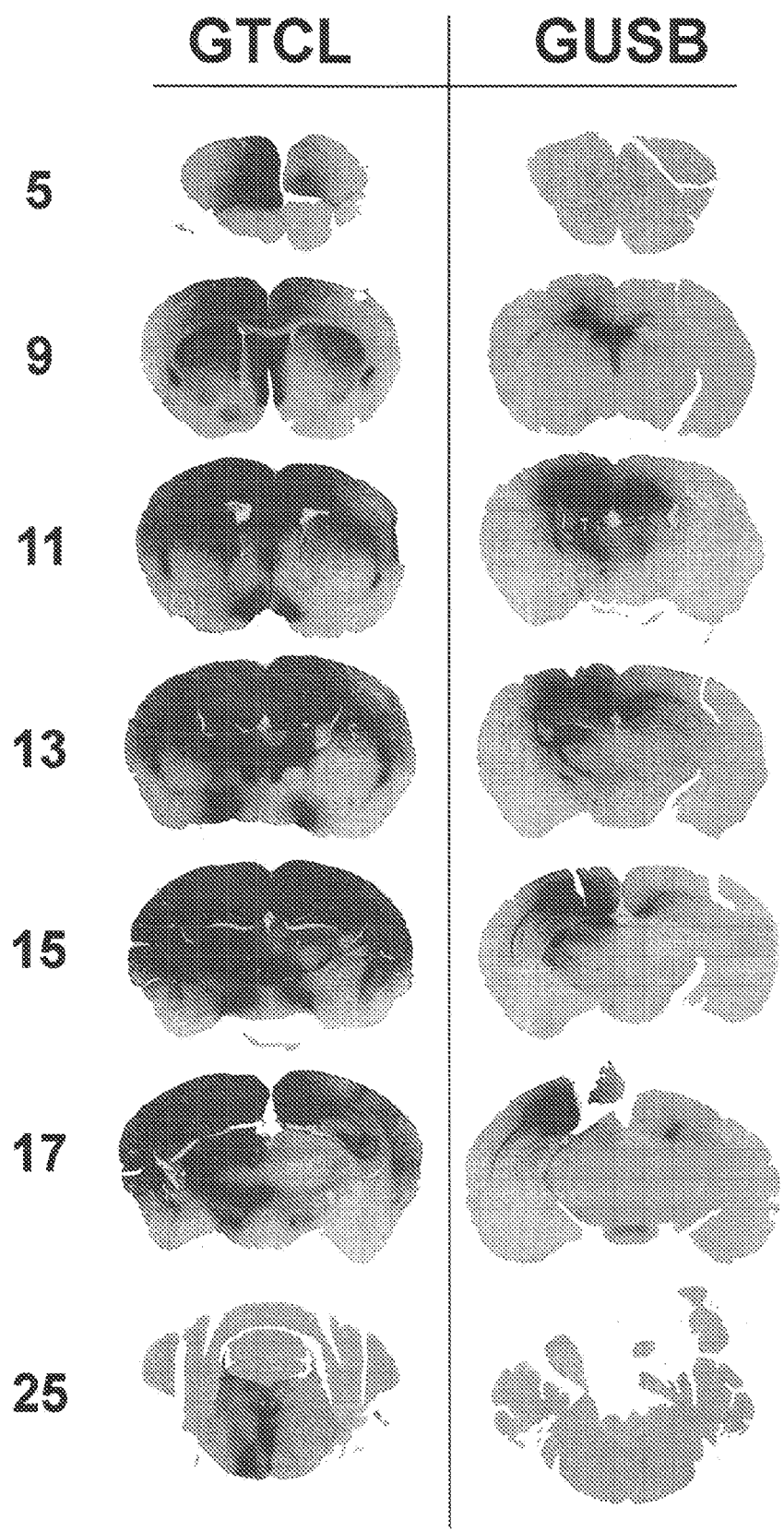
FIG. 6A provides in situ histochemical reactions showing expanded distribution of enzyme activity with GUSB-TTC. Numbers represent sections along the rostral-caudal axis.
Figure 6B:
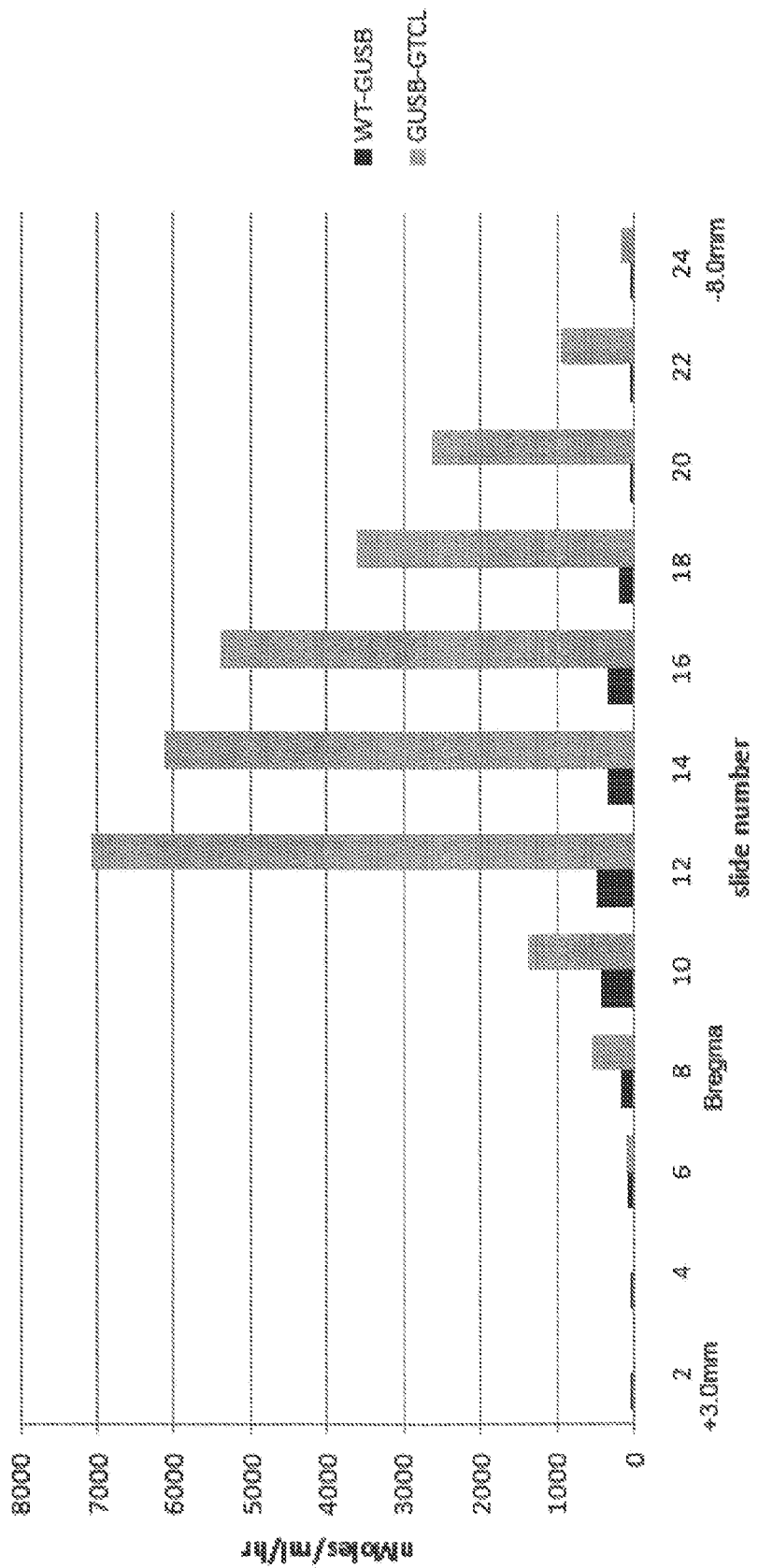
FIG. 6B provides a graph showing the total quantitative GUSB activity in the sections shown in FIG. 6A. Distances relative to Bregma show spread over most of brain by huGTCL. The injection site was at section 12.
Figure 7:
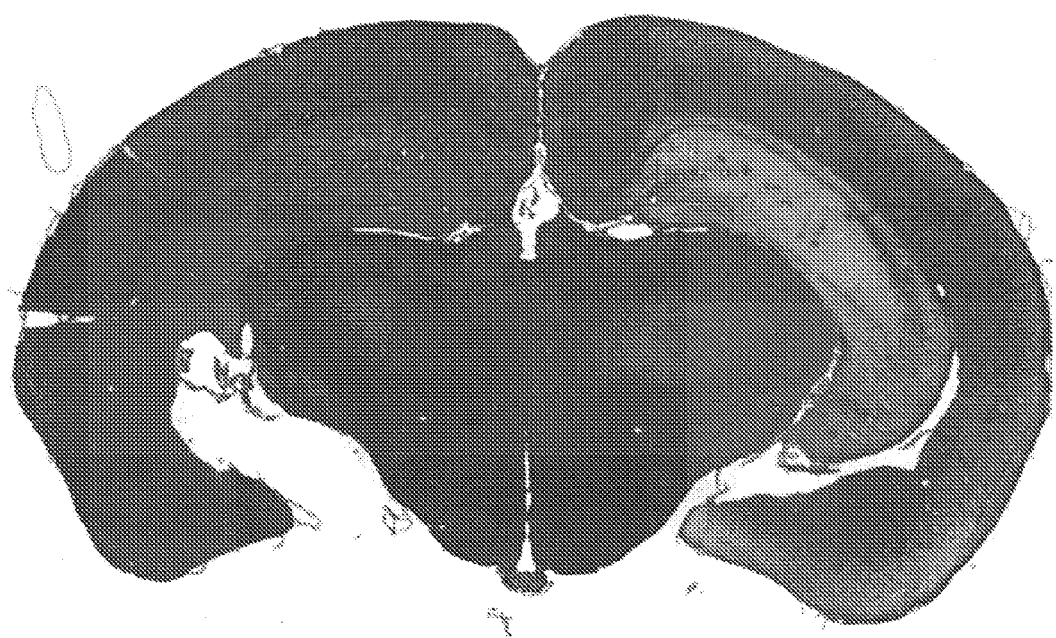
FIG. 7 provides an example of GUSB staining 3 months post-injection of AAV9-GUSB-huTTC.

The AAV1-GUSB-huTTC vector was injected into the hippocampus and compared to brains injected with an identical titer of vector expressing wild-type GUSB. The hippocampus was selected because the spread is limited and well understood (Passini et al. (2002) J. Neurosci., 22:6437-46; Cearley et al. (2006) Mol. Ther., 13:528-37). The results are shown in FIG. 6. There was significantly greater distribution of GUSB activity staining along the rostral-caudal axis of the brain (FIG. 6). FIG. 6 shows brains one month post-injection and the bar graph shows the quantitative increase in spread of enzymatic activity. At 3 months, sections of brain were completely stained positive for GUSB activity (FIG. 7). Although the level of GUSB activity is very high, a transgenic strain expressing the human GUSB on the mutant mouse background stains similarly in this assay (Kyle et al. (1990) Proc. Natl. Acad. Sci., 87:3914-8). Notably, the massive over-expression of GUSB in transgenic mice does not significantly affect the animal (Vogler et al. (2003) Proc. Natl. Acad. Sci., 100:2669-73).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated nucleic acid molecule comprising the nucleotide sequence having at least 90% homology to SEQ ID NO: 3.

2. An isolated nucleic acid molecule comprising the nucleotide sequence having at least 95% homology to SEQ ID NO: 3.

3. The isolated nucleic acid molecule of claim 1, wherein the nucleic acid molecule comprises SEQ ID NO: 3.

4. An isolated nucleic acid molecule encoding a fusion protein, wherein said fusion protein comprises humanized tetanus toxin fragment C (TTC) and a protein of interest, wherein said humanized TTC is encoded by the nucleic acid molecule of claim 1.

5. The nucleic acid molecule of claim 4, wherein the nucleic acid sequence encoding said humanized TTC is 3' and in frame to the nucleic acid molecule encoding the protein of interest.

6. The nucleic acid molecule of claim 4, wherein said humanized TTC and protein of interest are operably linked by an amino acid linker.

7. A vector comprising the nucleic acid molecule of claim 4.

8. The vector of claim 7, wherein the vector is a viral vector.

9. The vector of claim 8, wherein said viral vector is an adeno-associated virus.

10. The nucleic acid molecule of claim 4, wherein the protein of interest is a marker protein.

11. The nucleic acid molecule of claim 4, wherein the protein of interest is a therapeutic protein.

12. A composition comprising the vector of claim 7 and at least one pharmaceutically acceptable carrier.

13. The composition of claim 12, wherein the protein of interest is a therapeutic protein.

14. A method of treating a neurological disease or disorder, wherein said method comprises administering the composition of claim 13 to a patient in need thereof, wherein said therapeutic protein is for treating a neurological disease.

15. The method of claim 14, wherein said neurological disease or disorder is a lysosomal storage disease.

16. The method of claim 15, wherein the therapeutic protein is β-glucuronidase.

* * * * *

SEQUENCE LISTING

```
<160> NUMBER OF SEQ ID NOS: 4

<210> SEQ ID NO 1
<211> LENGTH: 1356
<212> TYPE: DNA
<213> ORGANISM: Clostridium tetani

<400> SEQUENCE: 1
aaaaatctgg attgttgggt tgataatgaa gaagatatag atgttatatt aaaaaagagt      60
acaattttaa atttagatat taataatgat attatatcag atatatctgg gtttaattca     120
tctgtaataa catatccaga tgctcaattg gtgcccggaa taaatggcaa agcaatacat     180
ttagtaaaca atgaatcttc tgaagttata gtgcataaag ctatggatat tgaatataat     240
gatatgttta ataattttac cgttagcttt tggttgaggg ttcctaaagt atctgctagt     300
```

| | |
|---|---|
| catttagaac aatatgacac aaatgagtat tcaataatta gctctatgaa aaaatatagt | 360 |
| ctatcaatag gatctggttg gagtgtatca cttaaaggta ataacttaat atggacttta | 420 |
| aaagattccg cgggagaagt tagacaaata acttttaggg atttatctga taaatttaat | 480 |
| gcttatttag caaataaatg ggttttata actattacta atgatagatt atcttctgct | 540 |
| aatttgtata taaatggagt acttatggga agtgcagaaa ttactggttt aggagctatt | 600 |
| agagaggata taatataac attaaaacta gatagatgta ataataataa tcaatacgtt | 660 |
| tctattgata aatttaggat attttgcaaa gcattaaatc caaagagat tgaaaaatta | 720 |
| tacacaagtt atttatctat aaccttttta agagacttct ggggaaaccc tttacgatat | 780 |
| gatacagaat attatttaat accagtagct tatagttcta aagatgttca attgaaaaat | 840 |
| ataacagatt atatgtattt gacaaatgcg ccatcgtata ctaacggaaa attgaatata | 900 |
| tattatagaa ggttatatag tggactaaaa tttattataa aaagatatac acctaataat | 960 |
| gaaatagatt cttttgttag atcaggtgat tttattaaat tatatgtatc atataacaat | 1020 |
| aatgagcaca ttgtaggtta tccgaaagat ggaaatgcct ttaataatct tgatagaatt | 1080 |
| ctaagagtag gttataatgc cccaggtatc cctctttata aaaaaatgga agcagtaaaa | 1140 |
| ttgcgtgatt taaaaaccta ttctgtacaa cttaaattat atgatgataa agatgcatct | 1200 |
| ttaggattag taggtaccca taatggtcaa ataggcaacg atccaaatag ggatatatta | 1260 |
| attgcaagca actggtactt taatcattta aaagataaaa cttaacatg tgattggtac | 1320 |
| tttgtaccta cagatgaagg atggacaaat gattaa | 1356 |

<210> SEQ ID NO 2
<211> LENGTH: 1402
<212> TYPE: DNA
<213> ORGANISM: Artificial Sequence
<220> FEATURE:
<223> OTHER INFORMATION: humanized tetanus toxin C fragment

<400> SEQUENCE: 2

| | |
|---|---|
| ggcggaggta ccgtcgacct cgaggaaaga acctggactg ctgggtggac aacgaggagg | 60 |
| acatcgacgt gatcctgaag aagagcacca tcctgaacct ggacatcaac aacgacatca | 120 |
| tcagcgacat cagcggcttc aacagcagcg tgatcaccta ccccgacgcc cagctggtgc | 180 |
| ccggcatcaa cggcaaggcc atccacctgg tgaacaacga gagcagcgag gtgatcgtgc | 240 |
| acaaggccat ggacatcgag tacaacgaca tgttcaacaa cttcaccgtg agcttctggc | 300 |
| tgagagtgcc caaggtgagc gccagccacc tggagcagta cgacaccaac gagtacagca | 360 |
| tcatcagcag catgaagaag tacagcctga gcatcggcag cggctggagc gtgagcctga | 420 |
| agggcaacaa cctgatctgg accctgaagg acagcgccgg cgaggtgaga cagatccacct | 480 |
| tcagagacct gagcgacaag ttcaacgcct acctggccaa caagtgggtg ttcatcacca | 540 |
| tcaccaacga cagactgagc agcgccaacc tgtacatcaa cggcgtgctg atgggcagcg | 600 |
| ccgagatcac cggcctgggc gccatcagag aggacaacaa catcaccctg aagctggaca | 660 |
| gatgcaacaa caacaaccag tacgtgagca tcgacaagtt cagaatcttc tgcaaggccc | 720 |
| tgaaccccaa ggagatcgag aagctgtaca ccagctacct gagcatcacc ttcctgagag | 780 |
| acttctgggg caaccccctg agatacgaca ccgagtacta cctgatcccc gtggcctaca | 840 |
| gcagcaagga cgtgcagctg aagaacatca ccgactacat gtacctgacc aacgccccca | 900 |
| gctacaccaa cggcaagctg aacatctact acagaagact gtacagcggc ctgaagttca | 960 |
| tcatcaagag atacaccccc aacaacgaga tcgacagctt cgtgagaagc ggcgacttca | 1020 |

| tcaagctgta cgtgagctac aacaacaacg agcacatcgt gggctacccc aaggacggca | 1080 |
| acgccttcaa caacctggac agaatcctga gagtgggcta caacgccccc ggcatccccc | 1140 |
| tgtacaagaa gatggaggcc gtgaagctga gagacctgaa gacctacagc gtgcagctga | 1200 |
| agctgtacga cgacaaggac gccagcctgg gcctggtggg cacccacaac ggccagatcg | 1260 |
| gcaacgaccc caacagagac atcctgatcg ccagcaactg gtacttcaac cacctgaagg | 1320 |
| acaagaccct gacctgcgac tggtacttcg tgcccaccga cgagggctgg accaacgact | 1380 |
| gactcgaggg aggcgccggc gg | 1402 |

<210> SEQ ID NO 3
<211> LENGTH: 1356
<212> TYPE: DNA
<213> ORGANISM: Artificial Sequence
<220> FEATURE:
<223> OTHER INFORMATION: humanized tetanus toxin C fragment

<400> SEQUENCE: 3

| aagaacctgg actgctgggt ggacaacgag gaggacatcg acgtgatcct gaagaagagc | 60 |
| accatcctga acctggacat caacaacgac atcatcagcg acatcagcgg cttcaacagc | 120 |
| agcgtgatca cctaccccga cgcccagctg gtgcccggca tcaacggcaa ggccatccac | 180 |
| ctggtgaaca acgagagcag cgaggtgatc gtgcacaagg ccatggacat cgagtacaac | 240 |
| gacatgttca acaacttcac cgtgagcttc tggctgagag tgcccaaggt gagcgccagc | 300 |
| cacctggagc agtacgacac caacgagtac agcatcatca gcagcatgaa gaagtacagc | 360 |
| ctgagcatcg gcagcggctg gagcgtgagc ctgaagggca caacctgat ctggaccctg | 420 |
| aaggacagcg ccggcgaggt gagacagatc accttcagag acctgagcga caagttcaac | 480 |
| gcctacctgg ccaacaagtg ggtgttcatc accatcacca cgacagact gagcagcgcc | 540 |
| aacctgtaca tcaacggcgt gctgatgggc agcgccgaga tcaccggcct gggcgccatc | 600 |
| agagaggaca acaacatcac cctgaagctg gacagatgca acaacaacaa ccagtacgtg | 660 |
| agcatcgaca gttcagaat cttctgcaag gccctgaacc ccaaggagat cgagaagctg | 720 |
| tacaccagct acctgagcat caccttcctg agagacttct ggggcaaccc cctgagatac | 780 |
| gacaccgagt actacctgat ccccgtggcc tacagcagca aggacgtgca gctgaagaac | 840 |
| atcaccgact acatgtacct gaccaacgcc ccagctaca ccaacggcaa gctgaacatc | 900 |
| tactacagaa gactgtacag cggcctgaag ttcatcatca agagatacac ccccaacaac | 960 |
| gagatcgaca gcttcgtgag aagcggcgac ttcatcaagc tgtacgtgag ctacaacaac | 1020 |
| aacgagcaca tcgtgggcta cccccaaggac ggcaacgcct tcaacaacct ggacagaatc | 1080 |
| ctgagagtgg gctacaacgc ccccggcatc cccctgtaca gaagatgga ggccgtgaag | 1140 |
| ctgagagacc tgaagaccta cagcgtgcag ctgaagctgt acgacgacaa ggacgccagc | 1200 |
| ctgggcctgg tgggcaccca caacggccag atcggcaacg accccaacag agacatcctg | 1260 |
| atcgccagca actggtactt caaccacctg aaggacaaga ccctgacctg cgactggtac | 1320 |
| ttcgtgccca ccgacgaggg ctggaccaac gactga | 1356 |

<210> SEQ ID NO 4
<211> LENGTH: 451
<212> TYPE: PRT
<213> ORGANISM: Clostridium tetani

<400> SEQUENCE: 4

Lys Asn Leu Asp Cys Trp Val Asp Asn Glu Glu Asp Ile Asp Val Ile
1               5                   10                  15

```
Leu Lys Lys Ser Thr Ile Leu Asn Leu Asp Ile Asn Asn Asp Ile Ile
            20                  25                  30

Ser Asp Ile Ser Gly Phe Asn Ser Val Ile Thr Tyr Pro Asp Ala
        35                  40                  45

Gln Leu Val Pro Gly Ile Asn Gly Lys Ala Ile His Leu Val Asn Asn
    50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Asp Thr Asn Glu Tyr Ser Ile
            100                 105                 110

Ile Ser Ser Met Lys Lys Tyr Ser Leu Ser Ile Gly Ser Gly Trp Ser
            115                 120                 125

Val Ser Leu Lys Gly Asn Asn Leu Ile Trp Thr Leu Lys Asp Ser Ala
        130                 135                 140

Gly Glu Val Arg Gln Ile Thr Phe Arg Asp Leu Ser Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
            180                 185                 190

Glu Ile Thr Gly Leu Gly Ala Ile Arg Glu Asp Asn Asn Ile Thr Leu
            195                 200                 205

Lys Leu Asp Arg Cys Asn Asn Asn Asn Gln Tyr Val Ser Ile Asp Lys
    210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255

Pro Leu Arg Tyr Asp Thr Glu Tyr Tyr Leu Ile Pro Val Ala Tyr Ser
            260                 265                 270

Ser Lys Asp Val Gln Leu Lys Asn Ile Thr Asp Tyr Met Tyr Leu Thr
    275                 280                 285

Asn Ala Pro Ser Tyr Thr Asn Gly Lys Leu Asn Ile Tyr Tyr Arg Arg
290                 295                 300

Leu Tyr Ser Gly Leu Lys Phe Ile Ile Lys Arg Tyr Thr Pro Asn Asn
305                 310                 315                 320

Glu Ile Asp Ser Phe Val Arg Ser Gly Asp Phe Ile Lys Leu Tyr Val
                325                 330                 335

Ser Tyr Asn Asn Asn Glu His Ile Val Gly Tyr Pro Lys Asp Gly Asn
            340                 345                 350

Ala Phe Asn Asn Leu Asp Arg Ile Leu Arg Val Gly Tyr Asn Ala Pro
            355                 360                 365

Gly Ile Pro Leu Tyr Lys Lys Met Glu Ala Val Lys Leu Arg Asp Leu
    370                 375                 380

Lys Thr Tyr Ser Val Gln Leu Lys Leu Tyr Asp Asp Lys Asp Ala Ser
385                 390                 395                 400

Leu Gly Leu Val Gly Thr His Asn Gly Gln Ile Gly Asn Asp Pro Asn
                405                 410                 415

Arg Asp Ile Leu Ile Ala Ser Asn Trp Tyr Phe Asn His Leu Lys Asp
            420                 425                 430
```

-continued

```
Lys Thr Leu Thr Cys Asp Trp Tyr Phe Val Pro Thr Asp Glu Gly Trp
        435                 440                 445
Thr Asn Asp
    450
```